United States Patent [19]

Demain et al.

[11] 4,248,966
[45] Feb. 3, 1981

[54] SYNTHESIS OF ISOPENICILLIN DERIVATIVES IN THE ABSENCE OF LIVING CELLS

[75] Inventors: Arnold L. Demain, Wellesley, Mass.; Toshio Konomi, Kobe, Japan; Jack E. Baldwin, Oxford, England

[73] Assignee: Massachusetts Institute of Technology, Cambridge, Mass.

[21] Appl. No.: 40,061

[22] Filed: May 17, 1979

[51] Int. Cl.$^3$ ............... C12P 37/00; C12R 1/75
[52] U.S. Cl. ............................. 435/43; 435/926
[58] Field of Search ........................... 435/43, 926

[56] References Cited

U.S. PATENT DOCUMENTS 4,002,530  1/1977  Troonen et al. ............... 435/43

OTHER PUBLICATIONS

Troonen et al., "RIT 2214, A New Biosynthetic Penicillin Produced by a Mutant of Cephalosporium Acremonium", in The Journal of Antibiotics, Dec. 1976, pp. 1258-1267.

Primary Examiner—Lionel M. Shapiro
Attorney, Agent, or Firm—Arthur A. Smith, Jr.; Robert J. Horn, Jr.; Anthony M. Lorusso

[57] ABSTRACT

Isopenicillin derivatives having antimicrobial properties and a general formula of:

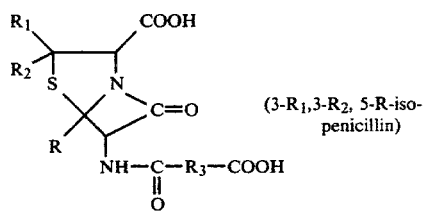

(3-R$_1$,3-R$_2$, 5-R-isopenicillin)

where R, R$_1$, and R$_2$ are hydrogen, methyl, ethyl, propyl, isopropyl, or halogenated methyl, ethyl, propyl or isopropyl radicals and R$_3$ is

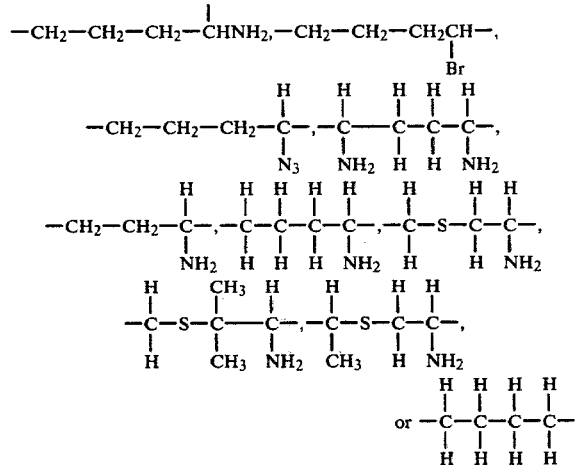

are produced in a cell-free system using an extract from *Cephalosporium acremonium*. The starting materials for the synthesis consist of tripeptides composed of unsubstituted or β-substituted D-valine, unsubstituted or substituted L cysteine, and L- α-aminoadipic acid or its analogues. Certain enzymes in the cell-free extract are inactivated so that conversion does not proceed past the isopenicillin stage.

10 Claims, No Drawings

SYNTHESIS OF ISOPENICILLIN DERIVATIVES IN THE ABSENCE OF LIVING CELLS

BACKGROUND OF THE INVENTION

This invention relates to a cell-free process for producing isopenicillin N and isopenicillin N derivatives.

Isopenicillin N is a water soluble β-lactam antibiotic having the formula:

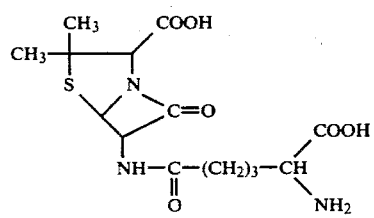

The aminoadipyl side chain is in the L-configuration in isopenicillin N. Penicillin N has a structure identical to isopenicillin N except that the aminoadipyl side chain is in the D-configuration.

Cell-free syntheses of penicillins and the related antibiotic cephalosporins are known in the art. A cell-free cephalosporin synthesis is disclosed in U.S. application Ser. No. 880,036 entitled Acellular Synthesis of Cephalosporins, filed Mar. 17, 1978, by A. L. Demain et al U.S. Pat. No. 4,178,210, issued Dec. 11, 1979. In *Synthesis of δ-(α-Aminoadipyl)cysteinylvaline And Its Role In Pencillin Biosynthesis*, Fawcett et al., Biochem. J. v. 157, p. 651 (1976), and *Aspects of Cephalosporin and Penicillin Biosynthesis*, Second Internat. Symp. Genetics of Industrial Microorganisms (K. D. MacDonald, ed) Academic Press, London, 1976, it is disclosed that δ(L-α-aminoadipyl)-L-cysteinylD-valine (hereinafter "LLD") can be converted by a cell-free extract to penicillin N.

SUMMARY OF THE INVENTION

In accordance with the invention, it has been discovered that certain cell-free extracts of *Cephalosporium acremonium* can synthesize isopenicillin N itself and a number of isopenicillin derivatives to the exclusion of penicillin N. The mechanism of reaction, broadly stated, is that the tripeptide δ(L-α aminoadipyl-L-cysteinyl-D-valine) undergoes ring formation resulting in the production of isopenicillin N provided that certain enzymes in the cell-free extract are inactivated so that the conversion does not go beyond the isopenicillin stage.

In addition to the foregoing, the cell-free system can catalyze the reactions when tripeptides containing certain synthetic β-substituted derivatives of L cysteine and of D valine and certain analogues of α-amino adipic acid are used in place of "LLD". Thus, the process of the invention is capable of producing isopenicillin derivatives which are entirely novel.

Examples of operable starting materials in the process of the invention include the following:

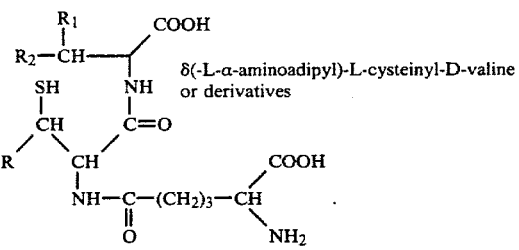

wherein, R, $R_1$, and $R_2$ are hydrogen, methyl, ethyl, propyl, or isopropyl or halogenated analogues of the foregoing radicals. When R is hydrogen and $R_1$ and $R_2$ are methyl groups, the resulting molecule is isopenicillin N itself.

By using analogues of α-aminoadipic acid, the amino adipyl side chain in the foregoing example may take on other configurations.

The formulas for α-aminoadipic acid and its analogues which are operable in the present invention are given below:

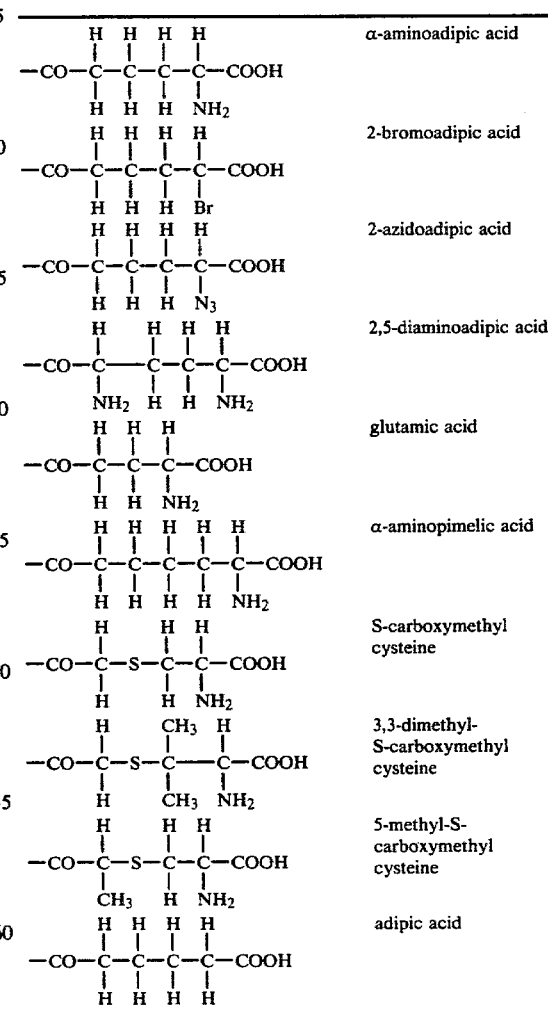

The synthesis is effected by contacting one of the foregoing starting materials with a cell-free extract in a reaction vessel in the presence of ATP. In a preferred process, R, $R_1$, and $R_2$ are hydrogen, or R is hydrogen, one of $R_1$ and $R_2$ is methyl or chloromethyl, and the other is selected from the group set forth above. Preferably, ATP and an ATP regeneration system comprising a phosphate donor and a phosphotransferase enzyme is also included in the reaction system. The preferred regeneration system comprises phosphoenolpyruvate and pyruvate kinase. The *C. acremonium* extract is preferably produced by lysing the cells or protoplasts thereof with lysing enzymes such as endo $\beta(1\rightarrow 3)$ glucanase, endo $\beta(1\rightarrow 4)$ glucanase, zymolyase and mixtures thereof. Prior to conversion, late enzyme(s) of the cell-free extract is inactivated so that conversion does not proceed beyond the isopenicillin stage. Inactivation may be accomplished by freezing and thawing the extract. As used herein "late enzymes" refer to enzymes that catalyze reactions in the latter part of a biosynthetic pathway.

Accordingly, objects of the invention include the provision of a method of producing novel isopenicillin derivatives and isopenicillin N in a cell-free system.

These and other objects and features of the invention will be apparent from the following description of some preferred embodiments.

DESCRIPTION OF THE PREFERRED EMBODIMENTS

At the outset, the invention is described in its broadest overall aspects with a more detailed description following. In accordance with the invention, a starting material comprising "LLD" or its derivatives is intimately contacted with a cell-free extract, made from *C. acremonium*, in the presence of ATP and is thereby transformed by enzymes in the extract to an isopenicillin derivative. *C. acremonium* is a well known microorganism, and several strains are available from the American Type Culture Collection under names such as ATCC 20339 (Cephalosporium sp. strain F. 12), ATCC 14553 (*C. acremonium*) and *Acremonium strictum* ATCC 35255. In accordance with the present invention, the conversion may be carried out with "non-producing" mutants of ATCC 36255 for example, those designated M-0198, M-0199 and M-1836. These mutants are blocked early, presumably in the formation of "LLD"; thus they do not produce antibiotics in the main culture medium. However, extracts prepared from these mutants can convert "LLD" to antibiotic. Thus if LLD or its derivatives are added, antibiotic production is achieved.

The preferred method of preparing the cell-free extract comprises lysing a protoplast pellet made from whole cells obtained from 40-70 hr. mycelia and treated with, e.g., *Cytophaga* lytic enzyme L₁ preparation and Zymolyase-5000. After treatment with the enzymes, the protoplast pellet suspension is centrifuged and gently homogenized. A second centrifugation enables separation of a supernatant liquid extract which may be used to produce the isopenicillins after late enzyme(s) has been inactivated. Thus, if a suitable starting material is mixed with this cell-free extract and ATP, an isopenicillin derivative-rich solution results.

The substances which are useful as starting materials include:

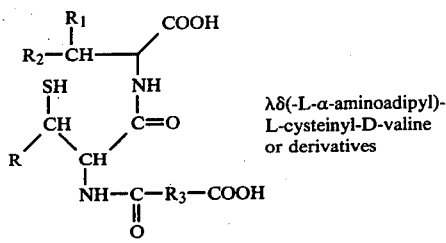

$\lambda\delta$(-L-$\alpha$-aminoadipyl)-L-cysteinyl-D-valine or derivatives

R, $R_1$, and $R_2$ can be hydrogen, methyl, ethyl, propyl or isopropyl or halogenated analogues of these radicals. $R_3$ is

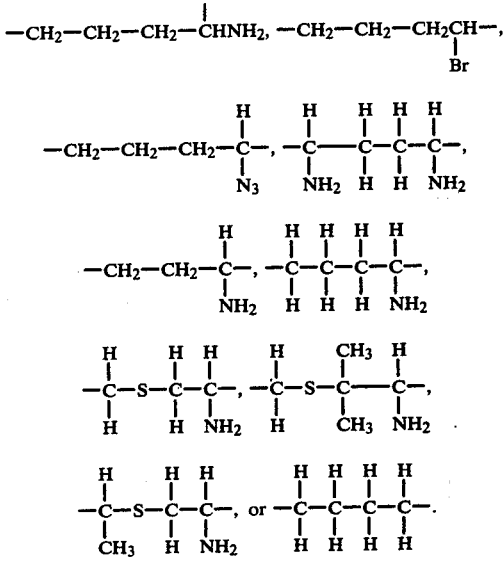

These tripeptides are converted, via ring formation, to isopenicillin derivatives of the formula given below when $\alpha$-aminoadipic acid or its analogue, one of which is included in the starting mixture:

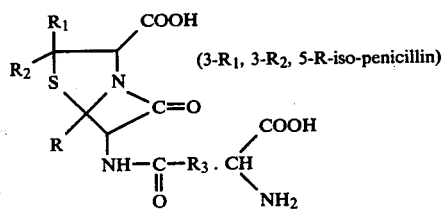

(3-$R_1$, 3-$R_2$, 5-R-iso-penicillin)

wherein R, $R_1$, $R_2$ and $R_3$ have the meaning set forth above.

Thus in addition to LLD containing $\alpha$-amino adipic acid, $\alpha$-AAA analogues can be used as starting materials to synthesize isopenicillin derivatives, such analogues include: L-2-bromoadipic acid, L-2-azidoadipic acid, L-2,5-diaminoadipic acid, adipic acid, L-glutamic acid, L-$\alpha$-aminopimelic acid, L-S-carboxymethylcysteine, L-3,3-dimethyl-S-carboxymethylcysteine and L-5-methyl-S-carboxymethylcysteine.

It has also been discovered that providing aeration by shaking and providing energy by the addition of ATP, and especially ATP plus an ATP regeneration system, increases the amount of isopenicillin produced. The ATP regenerating system comprises a phosphate donor and a phosphotransferase enzyme. The preferred donor is phosphoenolpyruvate and its corresponding phosphotransferase enzyme, pyruvate kinase. However, it will be appreciated that other phosphate donor phosphotransferase systems may also be used. These include but are not limited to phosphotransferases such as creatine kinase, acetate kinase, carbamate kinase, phosphoramidate kinase, arginine kinase, 3-phosphoglycerate kinase, and aspartate kinase, and corresponding phosphate donors such as creatine phosphate, acetyl phosphate, carbamyl phosphate, phosphoramidate, arginine phosphate, L-3-diphosphoglycerate, and aspartyl phosphate. Since the extract already contains some ATP, small quantities of antibiotic are produced even if no ATP is added to the system.

The presence of an isopenicillin can be verified with the aid of mutants of Escherichia coli (designated here Ess) or of Pseudomonas aeruginosa (designated here Pss) (see Agr. Biol. Chem., v. 38(9), 1761-1752, 1974) which are supersensitive specifically to $\beta$-lactam antibiotics. Also useful is penicillinase (Difco Laboratories), an enzyme which destroys the antibiotic properties of isopenicillin N and penicillin N. The cell-free system of the invention has been observed to produce antibiotic activity which is effective against E. coli Ess or P. aeruginosa Pss and thus contains the $\beta$-lactam moeity. Furthermore, the antibiotic activity of the product was destroyed by penicillinase. Accordingly, it is clear that a $\beta$-lactam antibiotic having the 5 membered thiazolidine ring was being produced. That the product obtained from the conversion of "LLD" is isopenicillin N and not penicillin N was verified by comparing the antibacterial properties of the synthesis product with the anti-bacterial properties of known samples of penicillin N and isopenicillin N against a series of Gram-positive and Gram-negative bacteria.

To differentiate isopenicillin N from penicillin N, the in vitro antibiotic activity is compared against two Gram-negative bacteria (Salmonella typhimurium ATCC 13311 and Pseudomonas aeruginosa strain Pss) and two Gram-positive bacteria (Staphylococcus aureus ATCC 25923 and Sarcina lutea ATCC 9341). It has been found that isopenicillin N is more active against the Gram-positive species than against the Gram-negative species. On the other hand, penicillin N is more active against the Gram-negative than against the Gram-positive bacteria. The product of the cell-free conversion of "LLD" is clearly more active against Gram-positive bacteria than against Gram-negative species and thus is isopenicillin N.

It is thus apparent that the cell-free extract contains specific enzymes which, when supplied with the starting material set forth above, can produce isopenicillins.

The invention will be further understood from the following non-limiting examples:

PREPARATION OF EXTRACT

A seed medium was prepared containing (per liter): 30 g corn steep liquor, 10 g glucose, 30 g starch, 5 g calcium carbonate. Forty ml of the medium adjusted to pH 6.8 were added to a 250 ml Erlenmeyer flask. One drop of methyl oleate was added from a 1 ml pipette and the flask was sterilized by autoclaving. After cooling, the seed flask was inoculated with 1 ml of C. acremonium suspension prepared by harvesting the mycelia from one slant culture with 5 ml of sterile water. The inoculated seed flask was incubated for 72 hours on a rotary shaker at 250 rpm with a 2 in. diameter orbit. The whole broth obtained was used to inoculate the main culture medium.

Main cultures of C. acremonium were incubated at 25° C. on the shaker at 250 rpm in 250 ml flasks containing 40 ml samples of a medium consisting of the ingredients set forth below. The specific C. acremonium strain used in these examples was a mutant of strain CW-19. Strain CW-19 was obtained from Eli Lilly and Co. and is available on an unrestricted basis under the designation Acremonium strictum ATCC 36255 from the American Type Culture Collection, Rockville, MD. The mutant, designated M-0198 is a strain which cannot produce penicillin N and cephalosporium C in fermentations and is available on an unrestricted basis from the Northern Regional Research Center, U.S. Dept. of Agriculture, Peoria, IL 61604 under the designation Cephalosporium acremonium NRRL-11418. It should be noted, however, that the invention is not limited to the use of a specific mutant of C. acremonium. Indeed, the parent strain designated ATCC 36255 is capable of producing isopenicillins.

| Cephalosporium acremonium Main Culture Medium | |
| --- | --- |
| Sucrose | 36.0 g |
| Glucose | 27.0 g |
| $(NH_4)_2SO_4$ | 7.5 g |
| Oleic acid | 1.5 g |
| Salt #1 | 7.5 ml |
| Salt #2 | 135.0 ml |
| L-Methionine | 3.0 g |

One liter of water was added to these ingredients and the pH was adjusted to 7.3–7.5. Salt #2 was made up of a 20 g/l solution of ferrous ammonium sulfate·$6H_2O$. Salt #1 comprised a mixture of the ingredients set forth below dissolved in enough water to make 1.8 liters of solution.

| Salt #2 | |
| --- | --- |
| $K_2HPO_4$ | 208.0 g |
| $KH_2PO_4$ | 204.0 g |
| $Na_2SO_4 . 10H_2O$ | 22.7 g |
| $MgSO_4 . 7H_2O$ | 4.8 g |
| $CaCl_2 . 2H_2O$ | 1.0 g |
| $ZnSO_4 . 7H_2O$ | 0.4 g |
| $MnSO_4 . H_2O$ | 0.4 g |
| $CuSO_4 . 5H_2O$ | 0.1 g |

The mycelium harvested from six flasks after 40–70 hours of fermentation was filtered and washed 2 times with 40 ml samples of distilled water. The damp-dry mycelium was resuspended in 40 ml of 0.05 M McIlvaine's citrate-phosphate buffer (pH 7.2) plus 0.01 M dithiothreitol and incubated for 1 hour at 28° C. with shaking at 150 rpm. After filtering and washing, the mycelium was resuspended in 40 ml of 0.05 M McIlvaine's buffer (pH 7.2) this time containing 1.0 M NaCl, 0.02 M $MgSO_4$, 160 mg of the lysing preparation Cytophaga lytic enzyme $L_1$, and 160 mg Zymolyase 5000 from Arthrobacter. Cytophaga lytic enzyme $L_1$ was obtained from BDH Chemicals, Poole, Dorset, U.K. In the U.S. it is sold by Gallard-Schlessinger Chem. Mfg. Corp., Carle Place, N.Y. 11514. The nature of the preparation of this enzyme is described in British Pat. No. 1,048,887. The lysing preparation was originally isolated from a culture medium of a microorganism temporarily designated $L_1$. This organism has been deposited in the National Collection of Industrial Bacteria in Aberdeen, Scotland, as N.C.I.B. 9497. Lytic enzyme $L_1$ has been described as having endo $\beta(1\rightarrow3)$ and endo $\beta(1\rightarrow4)$ glucanase activities (Biochemical Journal, Manners et al., Vol. 135, p. 11, 1973). Zymolyase-5000, (hereinafter zymolyase), was obtained from Kirin Brewery Co., Ltd., Takasaki, Gumma Pref, Japan. Zymolyase-5000 is an enzyme preparation produced by a submerged culture of *Arthrobacter luteus*. It lyses cell walls of viable fungi. As supplied by Kirin, Zymolyase-5000 contains the lytic enzyme and may also contain $\beta$-1,3 glucanase (EC3.2.1.39), mannanase, protease and acid phosphatase. The preparation of zymolyase has been described in *Archives of Biochemistry and Biophysics*, Kitamura et al., vol. 153, p. 403 (1972).

The suspension was incubated at 28° C. for 3 hours with shaking at 120 rpm and then centrifuged at 800 xg for about 10 minutes. The resulting pellet was washed twice with 20 ml of Tris buffer (pH 7.2, 0.05 M) containing 1.0 M sucrose, 0.01 M $MgSO_4$, and 0.01 M KCl. After the final centrifugation, the protoplast pellet was gently homogenized in a Teflon homogenizer at 4° C. After 6 ml of tris buffer (pH 7.2, 0.05 M) containing 0.65 M mannitol, 0.01 M $MgSO_4$ and 0.01 M KCl had been added, the suspension was centrifuged at 1000 xg for 10 minutes. The supernatant fluid was frozen and thawed. The frozen and thawed product represents the cell-free extract.

EXAMPLE 1

Isopenicillin N

Five $\mu$moles of adenosine triphosphate (ATP), 10 $\mu$moles of phosphoenol pyruvate, and 100 $\mu$grams of pyruvate kinase were incubated for three hours at 25° C. at a pH of 7.2 with 100 $\mu$g of "LLD" and 1.0 ml of mutant M-0198 extract produced in accordance with the procedure set forth above. The reaction mixture showed the presence of antibiotic activity equivalent to 2.3 $\mu$g/ml using the $\beta$-lactam antibiotic, cephalosporin C, as standard i.e. 2.3 units/ml. One unit of antibiotic activity is that which produces the same size inhibitory zone as does 1 $\mu$g of cephalosporin C.

The product showed no antibiotic zones when penicillinase was added to the assay medium indicating that a penicillin or isopenicillin type antibiotic has been produced.

EXAMPLE 2

Cell-free extract from *C. acremonium* M-0198 was produced as in example 1. Reaction mixtures were as in example 1 except they contained different concentrations of "LLD". Assay was as in Example 1, samples being taken at 0, 0.25, 0.5, 0.75, 1, 2, 3 and 5 hours.

| Added "LLD" $\mu$g/ml | Maximum Antibiotic Produced units/ml |
|---|---|
| 0 | no antibiotic zone |
| 50 | 0.7 |
| 100 | 1.2 |
| 200 | 1.6 |

The data show that the produced antibiotic activity increases as the concentration of substrate is increased.

EXAMPLE 3

The cell-free extract from Example 2 was frozen for 2 days, thawed and used in this example. The results indicate that the activity is stable in the freezer. All other conditions were as in Example 2.

| Added "LLD" $\mu$g/ml | Maximum Antibiotic Produced units/ml |
|---|---|
| 0 | no antibiotic zone |
| 50 | 1.0 |
| 100 | 1.5 |
| 200 | 2.0 |
| 400 | 2.2 |
| 800 | 2.2 |

EXAMPLE 4

The cell-free extract from Example 2 was frozen for 10 days, thawed and used in this example. The results indicate that shaking and the energy generating system moderately increase the activity. All other conditions were as in Example 2.

| Added "LLD" $\mu$g/ml | Shaking rpm | Energy Generating System | Maximum Antibiotic Produced units/ml |
|---|---|---|---|
| 0 | 240 | present | no antibiotic zone |
| 200 | 240 | present | 2.5 |
| 200 | 120 | present | 2.5 |
| 200 | none | present | 1.7 |
| 200 | 240 | absent | 2.0 |

EXAMPLE 5

The cell-free extract from Example 2 was frozen for 15 days, thawed and used. The results indicate that activity decreases with decreased concentration of cell-free extract and that activity of the extract can be eliminated by boiling. All conditions as in Example 2.

| Added "LLD" $\mu$g/ml | Amount of Extract ml | Treatment of Extract | Maximum Antibiotic Produced units/ml |
|---|---|---|---|
| 0 | 0.8 | none | no antibiotic zone |
| 200 | 0.8 | none | 1.7 |
| 200 | 0.6 | none | 1.4 |
| 200 | 0.4 | none | 1.1 |
| 200 | 0.2 | none | no antibiotic zone |
| 200 | 0 | none | no antibiotic zone |
| 200 | 0.8 | boiled 5 min | no antibiotic zone |

EXAMPLE 6

Cell-free extracts from *C. acremonium* M-0198 were obtained as in Example 1 except the cultures were grown for different times before extracts were prepared. The results indicate that a 44 hr culture provides a more active extract than older cultures. 200 $\mu$g "LLD" was added per ml and the time of incubation was 1 hour.

| Culture Age hr | Antibiotic Produced units/ml |
|---|---|
| 44 | 5.3 |
| 56 | 1.8 |
| 68 | 2.2 |

EXAMPLE 7

A cell-free extract of *C. acremonium* M-0198 was produced as in Example 1. The results show that the δ(L-α-aminoadipyl)-L-cysteinyl-L-valine (hereinafter "LLL") is not converted to an antibiotic.

| Added Peptide | Maximum Antibiotic Produced Units/ml |
| --- | --- |
| 200 μg/ml "LLD" | 1.5 |
| 100 μg/ml "LLL" | no antibiotic zone |
| 200 μg/ml "LLL" | no antibiotic zone |
| 400 μg/ml "LLL" | no antibiotic zone |
| 800 μg/ml "LLL" | no antibiotic zone |

EXAMPLE 8

A cell-free extract of *C. acremonium* M-0198 was produced as in Example 1 except that the growth period was 48 hours. The cell-free extract was incubated for 1 hour in the presence of 200 μg of "LLD" per ml plus ATP and the energy generating system. The antibiotic production amounted to 5.5 units/ml. The cell-free extract was then compared to authentic isopencillin N and penicillin N with respect to in vitro activity against two Gram-positive and two Gram-negative cultures. The isopenicillin N and penicillin N were prepared at 5 μg/ml activity as based on a chemical assay of the β-lactam ring, i.e. the hydroxylamine assay.

| Assay Organism | Gram Stain | Penicillin N 10 μg/ml | Isopenicillin N 10 μg/ml | Reaction Product |
| --- | --- | --- | --- | --- |
| *Staphylococcus aureus* ATCC 25923 | positive | — | + | + |
| *Sarcina lutea* ATCC 9341 | positive | — | + | + |
| *Salmonella typhimurium* ATCC 13311 | negative | + | — | — |
| *Pseudomonas aeruginosa* Pss | negative | + | — | — |

It can be seen from the above that penicillin N at the concentration used is active against the Gram-negative species but not against the Gram-positive species. Isopenicillin N and the reaction product are active against the Gram-positive species but not against the Gram-negative cultures. Thus, the antimicrobial activity of the product mixture resembles isopenicillin N more than penicillin N.

From the foregoing, it will be obvious to those skilled in the art that various modifications in the above described process can be made without departing from the spirit and scope of the invention. For example, isopenicillins are produced whether or not an ATP regeneration system is added to the cell-free extract. Furthermore, although phosphoenolpyruvte and pyruvate kinase are the preferred phosphate donor and phosphotransferase enzyme for use in regenerating the ATP which drives the cell-free synthesis, it is clear that many other phosphate donors and transferase enzymes are operable and in fact that no ATP regeneration system at all be necessarily employed.

In addition to these modifications, it will be obvious to those skilled in the art that methods of producing the cell-free extract other than by treating the cells as disclosed herein will be possible. Specifically, it will be within the skill of those in the art to utilize other lysing enzymes, and indeed, other non-enzymatic methods of lysing the cell walls to produce the extract. Also, it is contemplated that enzymatically active fractions of the extract may be isolated, which fractions will show increased activity and be more productive of isopenicillin antibiotics. Also it is contemplated that cells treated by permeabilization agents (e.g. dimethylsulfoxide, benzene, toluene, Triton X-100) will produce issopenicillin antibiotics.

The invention may be embodied in other specific forms without departing from the spirit or essential characteristics thereof. The present embodiment is therefore to be considered in all respects as illustrative and not restrictive, the scope of the invention being indicated by the appended claims rather than by the foregoing description, and all changes which come within the meaning and range of equivalency of the claims are therefore intended to be embraced therein.

We claim:

1. A process for producing an isopenicillin derivative which exhibits antimicrobial activity, said process comprising the steps of:

1. providing a starting material selected from the group consisting of:

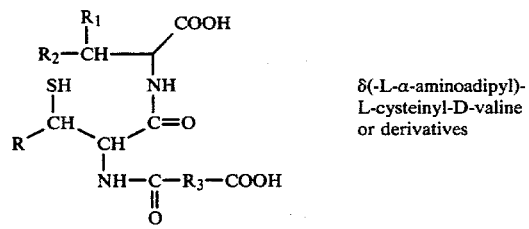

δ(-L-α-aminoadipyl)-L-cysteinyl-D-valine or derivatives wherein R, $R_1$, and $R_2$ are the same or different and are selected from the group consisting of hydrogen, methyl, ethyl, propyl, and isopropyl and $R_3$ is

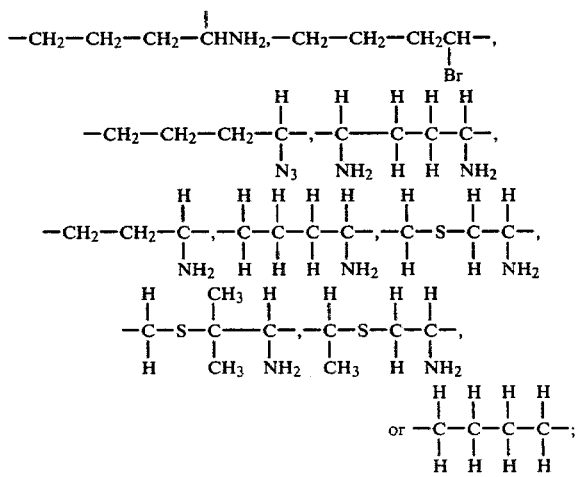

2. providing a cell-free extract or permeabilized cells of *Cephalosporium acremonium* containing a certain late enzyme(s) which has been inactivated so that the conversion cannot proceed beyond the isopenicillin stage;
3. contacting the extract and the starting material in a reaction vessel;
4. providing ATP as an energy source to said reaction; and
5. allowing a component of the extract to react with said starting material for a sufficient amount of time to produce an isopenicillin derivative of the formula:

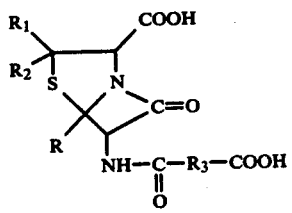

2. The process as set forth in claim 1 wherein R, $R_1$, and $R_2$ are hydrogen.

3. The process as set forth in claim 1 wherein R is hydrogen, one of $R_1$ and $R_2$ is methyl, and the other of $R_1$ and $R_2$ is selected from the group consisting of hydrogen, ethyl, propyl, and isopropyl.

4. The process as set forth in claim 1 wherein the ATP utilized is regenerated by an ATP regenerating system comprising a phosphate donor and a phosphotransferease enzyme.

5. The process as set forth in claim 4 wherein the phosphate donor is phosphoenolpyruvate and the phosphotransferase enzyme is pyruvate kinase.

6. The process as set forth in claim 1 wherein said cell-free extract is made by treating *Cephalosporium acremonium* cells with a lysing enzyme.

7. The process as set forth in claim 6 wherein said cell-free extract is made by treating *Cephalosporium acremonium* cells with endo $\beta(1\rightarrow 3)$ glucanase, endo $\beta(1\rightarrow 4)$ glucanase, and zymolyase.

8. The process as set forth in claim 1 wherein oxygen transfer is promoted by shaking the reaction components in the reaction vessel.

9. The process as set forth in claim 1 wherein mannitol and trace concentrations of KCl and $MgSO_4$ are included in the reaction and the system is buffered to about pH 7.2.

10. The process as set forth in claim 1 wherein, prior to step 3, said extract is frozen.

* * * * *